United States Patent [19]

Sakaguchi et al.

[11] 4,354,506
[45] Oct. 19, 1982

[54] INTRACRANIAL PRESSURE GAUGE

[75] Inventors: Iwao Sakaguchi, Ueda; Kunihiko Osaka, Nishinomiya; Shigenori Hokari; Kenichi Takahashi, both of Ueda, all of Japan

[73] Assignee: Naganokeiki Seisakujo Company, Ltd., Tokyo, Japan

[21] Appl. No.: 113,068

[22] Filed: Jan. 17, 1980

[51] Int. Cl.³ .................................................. A61B 5/00
[52] U.S. Cl. ...................................... 128/748; 73/729
[58] Field of Search ................... 128/672, 748, 903; 73/721, 728–729

[56] References Cited

U.S. PATENT DOCUMENTS

| | | | |
|---|---|---|---|
| 3,958,558 | 5/1976 | Dunphy et al. | 128/748 |
| 4,026,276 | 5/1977 | Chubbuck | 128/748 |
| 4,062,354 | 12/1977 | Taylor et al. | 128/748 |
| 4,127,110 | 11/1978 | Bullara | 128/748 |
| 4,206,762 | 6/1980 | Cosman | 128/748 X |
| 4,265,252 | 5/1981 | Chubbuck et al. | 128/748 |

OTHER PUBLICATIONS

Zervas, N. T. et al, "A Pressure-Balanced Radio-Telemetry System for the Measurement of ICP", Jrnl Neurosurgery V.47 Dec. 1977, pp. 899–911.

Primary Examiner—Kyle L. Howell
Assistant Examiner—Francis J. Jaworski
Attorney, Agent, or Firm—Birch, Stewart, Kolasch & Birch

[57] ABSTRACT

The present disclosure is directed to an intracranial pressure gauge which comprises a powerless resonance circuit composed of a coil and a condenser; a sensor equipped with a pressure-sensitive section capable, when implanted under the scalp, of changing either the inductance of the said coil or the capacitance of the said condenser in response to a change in intracranial pressure; and a grid dip meter capable of externally measuring the change in the resonance frequency of said sensor.

9 Claims, 5 Drawing Figures

INTRACRANIAL PRESSURE GAUGE

BACKGROUND AND SUMMARY OF THE INVENTION

The present invention relates to intracranial pressure guages and, more particularly to high precision gauges which are capable of measuring changes in intracranial pressure, not by physical connection with a wire or tube but by inductive coupling of a sensor implanted under the scalp with an external measuring device.

With conventional intracranial pressure gauges in use for chronic continuous measurment of changes in intracranial pressure of patients, the intracranial pressure has been directly measured by withdrawing signals from a sensor implanted under the scalp by means of a physical connecting material such as a wire or a tube. However, such gauges involve the risk of contamination from the outside because of the connecting material penetrating the scalp.

Some devices have been devised for the elimination of this disadvantage, for example, by connecting the sensor implanted under the scalp with an external measuring device such as by radio communication, and not by utilizing a physical connection. However, these devices have active circuits built in and accordingly are complex in structure, large in size, and tend to be involved in drift, etc. In addition, they employ component elements with such a low heat resistance that their sterilization cannot be achieved without resorting to incomplete and inefficient means such as gas application in place of heat application. Also, they cannot endure a long-term use since their built-in power source has a limited service life.

Conventional intracranial pressure gauges are, in general, implanted under the scalp separately from a shunt tube path. The shunt tube path is a separate catheter for discharging brain fluid with increased intracranial pressure to a point outside the brain cavity. This arrangement necessitates two catheters to be inserted into the ventricle. They require an additional tube path for the air release and clearing of the route within the sensor. Thus, they have the disadvantage that the size and volume of the device to be implanted under the scalp cannot be reduced very much.

Moreover, if air is sealed in the pressure-sensitive section of the sensor, the air pressure is caused to change with the changing temperature of the human body, which adversely affects the precise sensing of the intracranial pressure. It is possible to correct the intracranial pressure to adjust for the change in body temperature, but the correction for temperature is not practically available since the body temperature is more or less dependent on the location of measurement, and the change in intracranial pressure is too small for the application of the temperature correction technique.

Additionally, the intracranial pressure gauge requires high sensitivity up to atmospheric pressure in order to be capable of measuring an extremely small change in intracranial pressure relative to the atmospheric pressure.

The present invention has applied the principle of resonance grid dip to the solution of the above problems. According to this principle, when an induction-powered resonance circuit consisting of a coil and a condenser is implanted under the scalp, an external inductive coupling allows the resonance point for the implanted resonance circuit to be detected. An extensive investigation had led to the discovery that, when the induction-powered resonance circuit is made variable with respect to the inductance L (simply stated as L hereinafter) of its coil, to the capacitance C (simply stated as C hereinafter) of its condenser, or to both L and C and the relation has been established between the resonance frequency for L and C and the change in intracranial pressure, the above-mentioned inductive coupling may externally furnish indirect measurments of the intracranial pressure. The intended purpose of the present invention is achieved by inserting the sensor of the intracranial pressure gauge in the shunt tube path, thereby eliminating the dual tube paths, by evacuating the pressure-sensitive section of the sensor, thereby eliminating the bad effect of the included gas, if any, with temperature change, and by utilizing the beat phenomenon for detecting synthesized wave for detecting fine changes in intracranial pressure, thereby facilitating the measurement.

Accordingly, one of the objects of the present invention is to apply the concept of constituting a passive circuit without any built-in power source for making available a novel intracranial pressure gauge which consists of three components: (1) a powerless resonance circuit composed of a high-precision coil and condenser which is connected to an external measuring device by other means than physical connecting elements, resulting in no risk of contamination from the outside environment, a long-term availability, the applicability of thermal sterilization of the sensor prior to implantation, and an extremely reduced volume of the sensor; (2) a sensor equipped with a pressure-sensitive section capable, when implanted under the scalp, of changing either the L of the coil or the C of the condenser in response to the change in intracranial pressure; and (3) a grid dip meter capable of externally measuring the change in the resonance frequency of the sensor.

Another object of the present invention is to provide another type of intracranial pressure gauge which consists of three components: (1) a powerless resonance circuit composed of a coil and a condenser; (2) a sensor equipped with a pressure-sensitive section capable, when implanted under the scalp, of allowing the provided core to move within the coil as the change in intracranial pressure causes the bellows to change its length, thereby changing the L of the coil; and (3) a grid dip meter capable of externally measuring the change in the resonance frequency of the sensor.

Still another object of the present invention is to offer another type of intracranial pressure gauge which consists of three components: (1) a powerless resonance circuit, composed of a coil and a condenser, with increased sensitivity by making the magnetic path of the core continuous; (2) a sensor equipped with a pressure-sensitive section capable, when implanted under the scalp, of allowing the cylinder section of the provided core, in the form of a hat, equipped with a flange at the bottom side (brain side) of the cylinder section, to move within the coil as the change in intracranial pressure causes the provided metallic bellows to change its length, thereby changing its L; and (3) a grid dip meter capable of externally measuring the change in the resonance frequency of the sensor.

Still another object of the present invention is to offer another type of intracranial pressure gauge which consists of three components: (1) a powerless resonance circuit composed of a coil and a condenser, for which two shunt tube paths which communicate with each other make it possible to reduce the volume of the device to be implanted under the scalp and to release air and clear contaminations from the sensor; (2) a sensor equipped with a pressure-sensitive section capable, when implanted under the scalp, of changing either the L of the coil or the C of the condenser in response to the change in intracranial pressure and with a shunt tube path for discharging brain fluid from the ventricle, having the pressure-sensitive section inserted; and (3) a grid dip meter capable of externally measuring the change in the resonance frequency of the sensor. A still further object of the present invention is to offer another type of intracranial pressure gauge which consists of three components: (1) a powerless resonance circuit composed of a coil and a condenser; (2) a sensor equipped with a pressure-sensitive section capable, when implanted under the scalp, of changing either the L of the coil or the C of the condenser in response to the change in intracranial pressure conveyed via the meninges; and (3) a grid dip meter capable of externally measuring the change in the resonance frequency of the sensor.

Yet another object of the present inventon is to offer another type of intracranial pressure gauge which consists of four components: (1) a powerless resonance circuit composed of a coil and a condenser, which is capable of precise and easy measurement of fine changes in intracranial pressure; (2) a sensor equipped with a pressure-sensitive section capable, when implanted under the scalp, of changing the L of the coil in response to the change in intracranial pressure; (3) a grid dip meter capable of externally measuring the change in the resonance frequency of the sensor; and (4) a device capable of synthesizing the resonance frequency signal of the grid dip meter and the standard frequency signal.

Other objects and further scope of applicability of the present invention will become apparent from the detailed description given hereinafter; it should be understood, however, that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE INVENTION

The present invention will now be discussed in detail in connection with the drawings.

Figure 1:
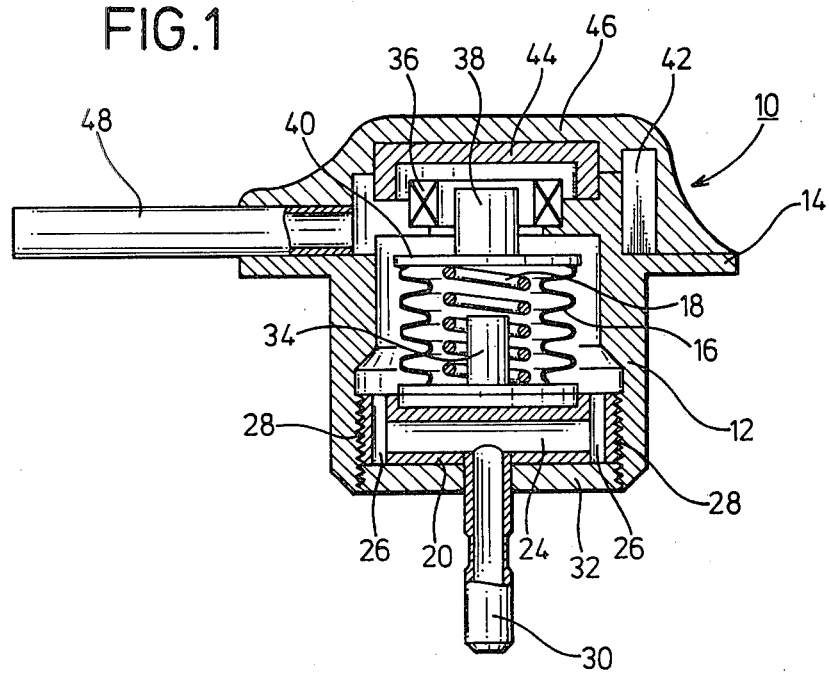
FIGS. 1 and 2 are cross-sectional views of the sensors 10 and 10a, respectively, of the present invention.

In FIG. 1, element 10 is the sensor of the present invention and element 12 is the sensor body in cylindrical form having the flange 14 provided slightly below its upper end. Element 16 is an encased bellows with its lower end fixed within the sensor body 12 and provided on the inside thereof with an auxiliary spring 18. A bellows base 20 catches the lower end edge of the bellows 16 at its upper disk well-dent. The communication hole 24, passing through the internal center of the bellows 20, is connected to the vertical groove 26 on both sides thereof. The disk has a screw thread 28 which is connected with the lower part of the sensor body 12 so as to move the disk vertically, thereby allowing a fine adjustment of the relative position of the coil to the core as will be described below.

Pipe 30, which is connected to the center of the bottom plane of the bellows base 20, communicates with the communication hole 24, and extends through the center of the mold part 32, sealing the lower end of the sensor body 12. Element 34 is the stopper which sets a positional limit on the contraction of the bellow 16. Element 36 is a coil which is fixed at the upper end section of the sensor body 12 with its center axis held in a vertical position. Element 38 is the ferrite core, which is formed in the shape of a hat by being provided with the flange 40 around its lower end section and which is attached vertically at the center of the upper free end of the bellows 16 so as to move within the coil 36 in response to the expansion and contraction of the bellows 16. Element 42 is a condenser which is combined with the coil 36 to constitute an induction-powered oscillator circuit. The coil 36 is covered with a cap 44 and further sealed with the mold 46 so that the upper plane of the sensor body 12 is completely covered.

Element 48 is a delivery tube. The brain fluid, introduced from the pipe 30, is passed successively through the communication hole 24 and the vertical groove 26 and around the bellows 16, until it is brought into contact with the core 38 and the coil 36 and then discharged through the delivery tube 48.

Figure 2:
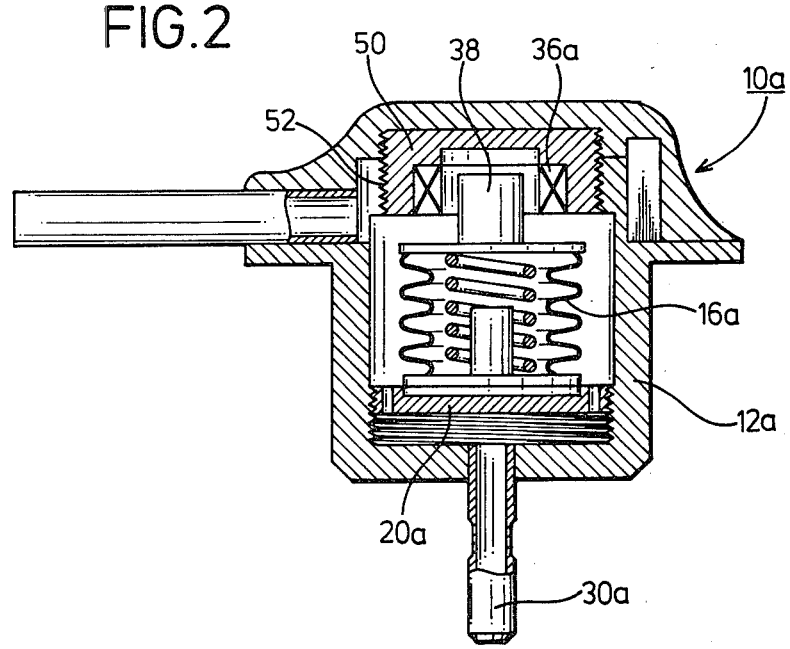

FIG. 2 is directed to a sensor 10a which concerns another embodiment of the present invention. This sensor is featured in that the introduction pipe 30a is extended from the center of the bottom of the sensor body 12a, the lower end section of the bellows 16a is fixed on the sensor body 12a via the bellows base 20a, and the coil 36a, fixed on the coil holder 50, is made vertically movable by combining the coil holder 50 with the upper section of the sensor body 12a by means of a screw 52 provided on the outer wall of the coil holder 50.

As described above, in the sensor 10 the vertical positioning of the core 38 within the coil 36 may be effected by adjusting the vertical position of the bellows base 20, while in the sensor 10a a similar positioning may be effected by not only adjusting the bellows base 20a but also by adjusting the vertical position of the coil holder 50. Therefore, it is possible to set the value of L for the coil to any appropriate standard level by preliminarily calibrating for the relative positional relationship between the coil and core.

Figure 3:
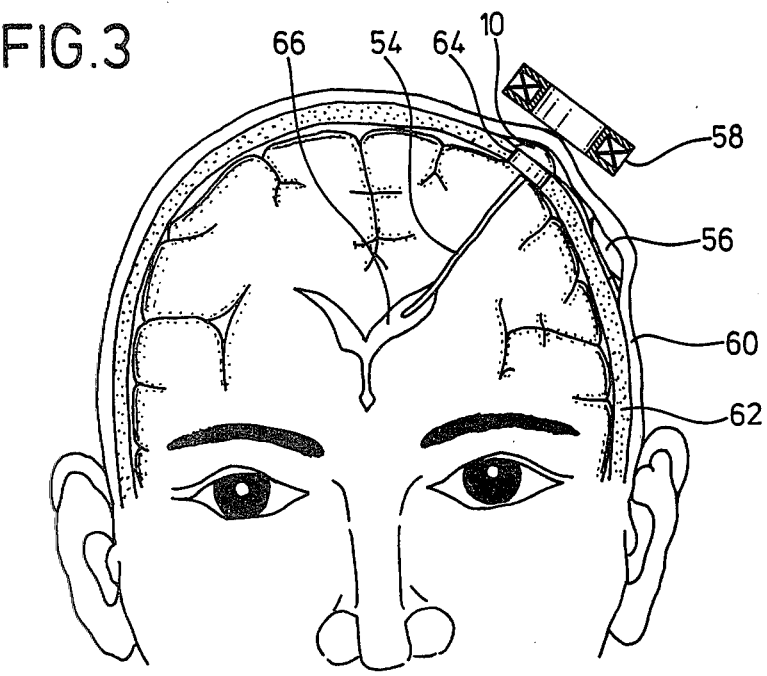
FIG. 3 illustrates the position of use of the device of the present invention.

For implantation of the sensor 10, as shown in FIG. 3, a well-dent 64 is made on the skull 62 under the scalp 60, and the sensor body 12 is inserted into this dent 64 until the flange 14 of the sensor body 12 comes into contact with the upper edge of the dent 64 on the skull 62.

The introduction pipe 30 has a catheter 54 connected at its end, which leads through the meninges into the ventricle. The delivery tube 48 is connected to the reservoir 56 serving for the discharge of brain fluid as well as for air release, and inserted into the shunt tube path as described later.

Element 58 is the oscillating coil of the grid meter, which is placed close to the sensor 10 over the scalp 60 to make inductive coupling with the sensor 10.

For actual application of the intracranial pressure gauge of the present invention, the sensor 10 is assembled after adjusting the bellows base 20 to set the relative positional relation between the coil 36 and the core 38 to the preliminarily determined standard position. The sensor is then mold-sealed, and implanted under the scalp 60 with connection to the ventricle 66. When some physiological causes lead to an increase in the quantity of brain fluid within the ventricle 66, the overflow fluid will be led via the shunt tube path into the atrium or abdominal cavity. However, if for some reason the shunt of the tube path is clogged, the brain fluid within the ventricle 66 will produce an anomalous pressure and the change in pressure thus caused propagates into the sensor 10 with the resulting contraction of the bellows 16. This contraction will in turn cause the core 38 to retreat within the coil 36, resulting in a change of L of the coil followed by a change in resonance frequency of the induction-powered resonance circuit within the sensor 10.

Now, if the oscillating coil 58 is placed close to the sensor 10 to produce resonance frequencies continuously changing within a certain range, and resonance will occur at the resonance point for the resonance frequency of the induction-powered resonance circuit. Therefore, it is possible to measure the intracranial pressure externally and indirectly if preliminarily information is obtained on the correspondence between the resonance point and the intracranial pressure.

The sensor 10 is thus capable of setting the pressure-sensitive section in the shunt tube path which discharges brain fluid from the vehicle. This is also the case with the sensor 10a.

Figure 4:
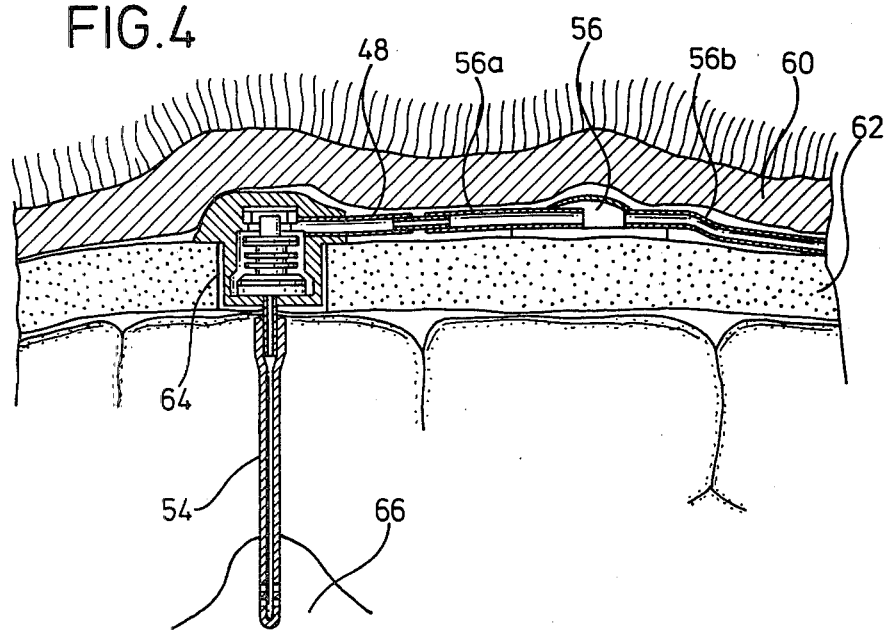
FIG. 4 is a cross-sectional view showing the application of the sensors 10 and 10a, implanted under the scalp.

FIG. 4 illustrates with magnification the case of setting the sensor 10 or 10a in the shunt tube path. Element 56 is a reservoir positioned next to the sensor 10 or 10a, element 56a is the connecting tube between the sensor delivery-tube 48 and the reservoir 56, and element 56b is the connecting tube attached to the reservoir 56. The reservoir 56 serves as a pumping space. The connecting tube 56a has its end section inserted slightly into the reservoir 56. Thus, when the reservoir 56 is pressed with a finger from outside the scalp, the inserted section of the connecting tube 56a is also pressed, thus acting as a nonreturn valve with a pumping effect.

On the other hand, when, with the connecting tube 56b is pressed with a finger, the reservoir 56 is pressed to a place apart from the inserted section of the connecting tube 56a, and the brain fluid is caused to flow in the reverse direction. Therefore, in case the sensor route should happen to be clogged, such a problem can be detected by the touch by pressing with a finger, and the sensor route may be cleared by pressing the reservoir 56 with an increased finger pressure.

Figure 5:
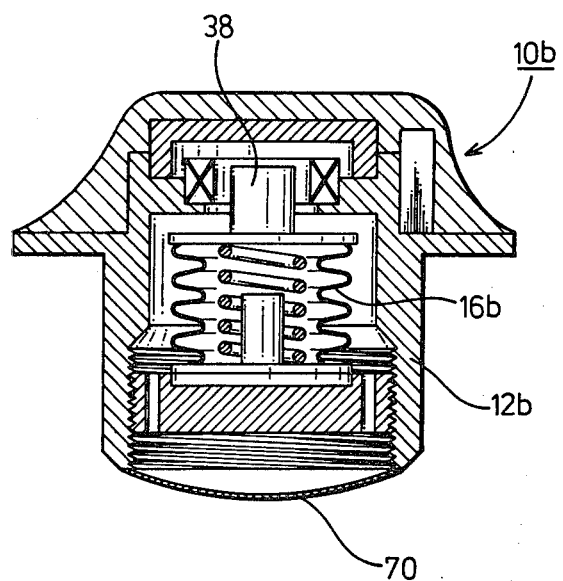
FIG. 5 is a cross-sectional view of another embodiment (10b) of the sensor of the present invention.

FIG. 5 shows a sensor 10b which represents another embodiment of the present invention, which is designed so that the bellows 16b is surrounded with a pressurizable medium such as silicone oil and the lower open section of the sensor body 12b is closed with a diaphragm 70 which is positioned in contact with the meninges for pressure sensing. With the sensor 10b it is unnecessary to provide a pipe for extending through the meninges to the ventricle. However, since the sensor 10b is closed by the diaphragm 70, it is impossible to insert this sensor 10b in the shunt tube path as sensors 10 and 10a.

In all the sensors 10, 10a and 10b, the core 38 is molded in the form of a hat, i.e., a cylinder with flange 40 provided at its lower end. The adoption of this form of hat is for reinforcing the magnetic path of the oscillating coil 58. The bellows 16 supporting the core 38 requires air-tightness and a high spring elasticity and therefore is made of a metal such as stainless steel or nickel. Without the adoption of the hat form, the use of such a metal would result in a cut-off of the magnetic path of the oscillating coil 58 with decreased pressure sensitivity.

There is a vacuum provided inside the sensor bellows 16 and it therefore follows that no problem results from the pressure-sensitive section being involved in an error due to the effect of a change in the temperature of the human body on the included gas in the bellows 16. In addition, the bellows 16 is made highly flexible to meet the need for sensing fine changes in pressure exerted upon the pressure-sensitive section. Thus, the bellows 16 is provided with the stopper device since any excess pressures placed on the bellows might cause permanent deformation.

The intracranial pressure is normally about 200 mmAq in gauge pressure, so that the intracranial pressure gauge is set for a considerably narrow range of approximately (+) 1000 mmAq to (−) 500 mmAq. A pressure change in this rangee causes too small a change in the length of the bellows and therefore is too small a change in L for a measurement to be made.

This difficulty in conducting measurements has been overcome by combining the resonance frequency of the sensor with a fixed frequency close to this resonance frequency and detecting the pressure change with magnification as a beat having the difference between both of the frequencies as a frequency of its own.

The value furnished by this measurement is an absolute pressure and accordingly a correction with subtraction of the measured value by the barometric oscillator may give the gauge pressure.

In the above examples, a bellows is used as the pressure-sensitive section, and its change in length is converted into a movement of the core within the coil, and finally the change in intracranial pressure is measured as the change in L of the coil. However, it is possible to make the condenser variable, utilizing the change in C of the condenser for the measurement, or to make both L and C simultaneously variable.

With the intracranial pressure gauges from the present invention, there is no possibility of contamination from the outside environment since the sensor under the scalp is in inductive coupling with an external measuring device; the sensor may endure a long-term use since it needs no built in power source; the sensor is highly resistant to heat and may be sterilized completely and efficiently by a thermal sterilizing treatment before being implanted under the scalp since it contains no active circuit; and the volume of the sensor may be substantially reduced.

When the pressure-sensitive section of the sensor is inserted in the shunt tube path, only one catheter suffices to be inserted into the ventricle, and the shunt tube path may be utilized for both air release and clearing, which is effective for reducing the quantity of implanted parts under the scalp. When the pressure-sensitive section has a vacuum with no gas included therein, no change in the temperature of the human body results in measurement errors.

On the other hand, with those devices which make use of a change in the relative position between the coil and the core, the shaping of the core in a hat form has effectively prevented the cut-off of the magnetic path, with an increased sensitivity of the pressure-sensitive section, and has been very effective for making practically available and highly reliable those intracranial pressure gauges which have not been available for small changes in intracranial pressure.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:
1. An intracranial pressure gauge which comprises,
a powerless resonance circuit composed of a coil and a condenser;
a sensor equipped with a pressure-sensitive section including an evacuated bellows which is capable, when implanted under the scalp, of changing the inductance of the said coil in response to a change in the length of the evacuated bellows with changing intracranial pressure; and
a grid dip meter capable of externally measuring the change in the resonance frequency of the said sensor.

2. An intracranial pressure gauge according to claim 1, wherein an introduction pipe is operatively connected to said sensor to transmit fluid from an individual's ventricle to said sensor to extend and contract said evacuated bellows in response to intracranial pressure in the ventricle.

3. An intracranial pressure gauge according to claim 2, wherein a delivery tube is operatively connected to said sensor to discharge brain fluid therefrom.

4. An intracranial pressure gauge according to claim 3, wherein a reservoir is operatively connected to a discharge end of said delivery tube for retaining a quantity of brain fluid.

5. An intracranial pressure gauge which comprises,
a powerless resonance circuit composed of a coil containing a core member and a condenser, said core member being attached to an evacuated bellows;
a sensor equipped with a pressure-sensitive section capable, when implanted under the scalp, to operatively permit said core to move within the said coil as the change in intracranial pressure causes the said evacuated bellows to change its length, thereby changing the inductance of the said coil; and
a grid dip meter capable of externally measuring the change in the resonance frequency of the said sensor.

6. An intracranial pressure gauge which comprises,
a powerless resonance circuit composed of a coil containing a core member having a cylinder section, and a condenser, said core member being attached to an evacuated bellows;
a sensor equipped with a pressure-sensitive section capable, when implanted under the scalp, to operatively permit said cylinder section of the provided core to move within the said coil as the change in intracranial pressure causes the provided evacuated bellows to change its length, thereby changing its inductance; and
a grip dip meter capable of externally measuring the change in the resonance frequency of the said sensor.

7. The intracranial pressure gauge of claim 6 wherein the core is in the form of a hat provided with a flange at the bottom of said cylindrical section, a free end of said evacuated bellows being fixed to said core and said flange being in abutment with said evacuated bellows;
said sensor being equipped with a pressure-sensitive section capable, when implanted under the scalp, of changing the inductance of the said coil in response to the change in intracranial pressure and including a shunt tube path for discharging brain fluid from an individual's ventricle, having the said pressure-sensitive section inserted therein.

8. An intracranial pressure gauge which comprises,
a powerless resonance circuit composed of a coil and a condenser;
a sensor equipped with a pressure-sensitive section including an evacuated bellows which is capable, when implanted under the scalp, of changing the inductance of the said coil in response to a change in the length of the evacuated bellows with changing intracranial pressure conveyed via the meninges, and
a grid dip meter capable of externally measuring the change in the resonance frequency of the said sensor.

9. An intracranial pressure gauge which comprises,
a powerless resonance circuit composed of a coil and a condenser;
a sensor equipped with a pressure-sensitive section including an evacuated bellows which is capable, when implanted under the scalp, of changing the inductance of the said coil in response to the change in the length of said evacuated bellows with changing intracranial pressure;
a grid dip meter capable of externally measuring the change in the resonance frequency of said sensor; and
a device capable of synthesizing the resonance frequency signal of the said grid dip meter and the standard frequency signal.

* * * * *